(12) United States Patent
Yokomizo et al.

(10) Patent No.: US 7,438,821 B2
(45) Date of Patent: Oct. 21, 2008

(54) LIQUID FILTERING METHOD AND FILTERING SYSTEM

(75) Inventors: Tomohisa Yokomizo, Oita (JP); Yukihiko Uchi, Fuji (JP)

(73) Assignee: Asahi Kasei Medical Co., Ltd., Tokyo (JP)

( * ) Notice: Subject to any disclaimer, the term of this patent is extended or adjusted under 35 U.S.C. 154(b) by 235 days.

(21) Appl. No.: 10/474,805

(22) PCT Filed: Apr. 2, 2002

(86) PCT No.: PCT/JP02/03313

§ 371 (c)(1),
(2), (4) Date: Oct. 14, 2003

(87) PCT Pub. No.: WO02/083200

PCT Pub. Date: Oct. 24, 2002

(65) Prior Publication Data

US 2004/0149657 A1 Aug. 5, 2004

(30) Foreign Application Priority Data

Apr. 13, 2001 (JP) .............................. 2001-116216

(51) Int. Cl.
B01D 37/00 (2006.01)
B01D 29/00 (2006.01)
A61M 1/02 (2006.01)
A61M 1/36 (2006.01)

(52) U.S. Cl. ........................ 210/804; 210/741; 210/767; 210/800

(58) Field of Classification Search .................. 210/85, 210/90, 97, 252, 254, 257.1, 258, 416.1, 210/455, 483, 637, 741, 767, 800, 804

See application file for complete search history.

(56) References Cited

U.S. PATENT DOCUMENTS

| 4,276,170 | A | * | 6/1981 | Vaillancourt | 210/436 |
| 5,069,792 | A | * | 12/1991 | Prince et al. | |
| 5,451,321 | A | * | 9/1995 | Matkovich | 210/641 |
| 5,591,337 | A | * | 1/1997 | Lynn et al. | 210/489 |
| 5,690,815 | A | * | 11/1997 | Krasnoff et al. | 210/97 |
| 5,779,902 | A | * | 7/1998 | Zuk, Jr. | 210/436 |
| 6,601,740 | B1 | * | 8/2003 | Clive | 210/435 |
| 6,610,710 | B2 | * | 8/2003 | Tanaka et al. | 514/330 |

FOREIGN PATENT DOCUMENTS

| EP | 0 526 678 A1 | | 2/1993 |
| EP | 0 958 838 A2 | * | 11/1999 |
| JP | 07-267871 | | 10/1995 |
| JP | 11-216179 | | 8/1999 |
| WO | 95/17236 | | 6/1995 |
| WO | 00/62891 | * | 10/2000 |

\* cited by examiner

*Primary Examiner*—John Kim
(74) *Attorney, Agent, or Firm*—Young & Thompson

(57) ABSTRACT

A filtering method which prevents adhesion between an outlet vessel and a filter element and which uses a flexible filter which allows smooth flow of liquid and is superior in filtering performance; and a filtering system. A filtering method which uses a flexible vessel having an inlet and an outlet for liquid, a sheet-like filter element, and a filter in which the inlet and outlet for liquid are separated by the filter element, wherein in filtering a liquid by the action of gravity or of a liquid feed pump, the pressure in the outlet of the filter is not less than 0 mmHg with respect to the atmospheric pressure; and a filtering system. Further, a filtering method in which a suitable combination of the filter and the hydrodynamic characteristics of the flow channel upstream or downstream of the filter is selected to make the pressure in the outlet of the filter not less than 0 mmHg with respect to the atmospheric pressure; and a filtering system.

7 Claims, 1 Drawing Sheet

LIQUID FILTERING METHOD AND FILTERING SYSTEM

TECHNICAL FIELD

The present invention relates to a liquid filtering method and to a filtering system for removing undesirable components such as aggregates and leukocytes from a liquid such as blood. In particular, the present invention relates to a filtering method for blood and a filtering system for blood for removing micro aggregates and leukocytes which may cause blood transfusion side effects from whole blood products, red cell products, platelet products, plasma products, and the like used for blood transfusion.

BACKGROUND ART

Whole blood collected from a donor is used for transfusion, as is, only in rare cases, but is commonly separated into components, such as a red cell product, platelet product, plasma product, and the like to be stored for transfusion. Since micro aggregates and leukocytes contained in these blood products cause various side effects after transfusion, these undesirable components are often removed before the blood products are used for transfusion. The need of removing the leukocytes has been widely recognized in recent years, and some European countries legislate the blood products to use for transfusion after applying a treatment for removing leukocyte.

The most common method of removing leukocytes from blood products is by processing blood products using a leukocyte-removing filter. Conventionally, blood products have been processed using a leukocyte-removing filter in many cases at the bedside when blood transfusion is performed. In recent years, however, to improve quality control of leukocyte reduced products and efficiency of leukocyte removal operations, it is more common to process the blood in blood centers before storing the blood products.

A blood collecting and separation set composed of two to four flexible bags, guide tubes for connecting the bags, an anticoagulant, a red cell preservative solution, and blood collecting needles has been used for collecting the blood from a donor, separating the blood into plural blood components, and storing each blood component. A system called a "closed system" or an "integrated system", in which the leukocyte-removing filter is integrated into the blood collecting-separation set, is widely used as a system that can be favorably used for "prestorage leukocyte reduction".

Such a system is disclosed in Japanese Patent Application Laid-open No. 01-320064, WO 92/20428, and the like.

While a filter comprising a filter element made of a non-woven fabric or a porous material packaged in a hard housing such as polycarbonate has been widely used for conventional leukocyte removing filters, it has been a problem that a steam sterilization process that is widely used for sterilization of the blood collecting-separation set can be applied to the filter only with difficulty since the housing has low gas permeability. The closed systems include a system in which the leukocytes are first removed from the whole blood product after collecting the blood, followed by removing the leukocyte removing filter to subject the system to centrifugation for separating each component, and a system in which the leukocytes are removed after separating the whole blood into plural blood components by centrifugation. In the latter case, however, the leukocyte-removing filter is subjected to centrifugation together with the blood collecting and separation set. In this instance, a hard may damage bags and tubes, or the housing itself may not withstand the stress and may be damaged during centrifugation.

To solve this problem, flexible leukocyte-removing filters, in which the housing is made of the same or a similar material having superior flexibility and high vapor permeability as used for the bags of the blood collecting -separation set, have been developed.

These filters are broadly classified into the type in which the filter elements are welded to a sheet-like flexible frame, which is then welded to a housing material (European Patent Publication No. 0 526 678, Japanese Patent Application Laid-open No. 11-216179) and the type in which the flexible housing is directly welded to the filter elements (Japanese Patent Application Laid-open No. 7-267871, WO 95/17236). The former type may be hereinafter called the frame welding type and the latter may be called the housing welding type.

When processing blood in these types of leukocyte-removing filters, the bag containing a blood product to be processed, connected to the blood inlet port of the filter via a tube, is placed at a height 20-100 cm higher than the filter to allow the blood product to pass through the filter by gravity. After filtration, the blood product is stored in a recovery bag connected to the blood outlet port of the filter via a tube. During filtration, a pressure loss is caused due to the resistance of the filter element, whereby the pressure in the space on the inlet side of the filter is maintained positive with respect to the atmospheric pressure. In the case of the filter attached to a flexible housing, the flexibility of the housing itself makes the housing swell like a balloon due to the positive pressure, thereby pressing the filter element against the outlet port side housing.

The bag for filling blood processed by the filter is usually placed at a height 50-100 cm lower than the filter. Since the blood flows in the flow channel on the downstream side by gravity, the pressure on the outlet side of the filter tends to become negative. For this reason, the flexible housing tends to adhere to the filter element. Specifically, because the filter element in the filter using a flexible housing tends to be caused to adhere to the housing on the outlet port side due to the double forces, the blood flow is obstructed, resulting in difficulty in ensuring a sufficient flow rate. This has been a longstanding problem.

Various countermeasures for this problem have been proposed in the past. Typical countermeasures include a method of inserting a soft polyvinyl chloride tube called a "connecting rod" between the filter element and outlet port side housing to prevent adhesion (EP 0 526 678), a method of preventing the adhesion by providing irregularities with a depth of 0.2 to 2 mm on the internal surface of the soft housing (Japanese Patent Application Laid-open No. 11-216179), and a method of inserting a screen made of knit fiber (WO 95/17236). However, as described in Japanese Patent Application Laid-open No. 11-216179, the method of inserting a connecting rod or a screen has been considered to have a risk of inducing defective welding of the housing if the other materials are inserted. Another problem of this method is an increase in the production cost due to the complicated process and use of extra materials.

In addition, if a connecting rod is used, the effect of preventing adhesion may be limited to the neighborhood of the connecting rod. Thus, the method of using a connecting rod may not provide a satisfactory effect. The method of providing irregularities on the internal surface of the housing disclosed in Japanese Patent Application Laid-open No.11-216179 has been proposed as a countermeasure for solving the problem in the method of inserting a connecting rod or a screen. When the housing material is directly welded to the filter element, however, the method has a risk of welding failure due to irregularities on the internal surface and may decrease the pressure resistance of the housing. Therefore, the application of this method was limited to the frame welding type filter.

In this manner, conventional technologies to prevent the adhesion of the housing on the outlet port side with the filter element due to negative pressure produced on the outlet side have been based on the means of providing a spacer with a clearance that can function as a flow channel for blood between the housing and the filter. This approach has not necessarily been successful.

DISCLOSURE OF THE INVENTION

An object of the present invention is to provide a method for filtering a liquid through a filter using a flexible housing, while preventing adhesion of the housing on the outlet side with the filter element, thereby avoiding a disturbed flow of liquid. A more specific object of the present invention is to provide a method for filtering a liquid through a filter using a flexible housing that can achieve the above object without providing a spacer to prevent adhesion of the housing on the outlet side with the filter element, accordingly without causing a risk of failure due to welding, without making the production process complicated, and without increasing costs.

Another object of the present invention is to provide a filtering system of a liquid through a filter using a flexible housing, while preventing adhesion of the housing on the outlet side with the filter element, thereby avoiding a disturbed flow of liquid.

As a result of extensive study to achieve the above objects, the inventors of the present invention have found that in a filter using a flexible housing, adhesion of the housing on the outlet port side with the filter element can be avoided without providing a spacer or the like, if the pressure at the filter outlet side is maintained positive, specifically 0 mmHg or more above atmospheric pressure.

To find the conditions that can ensure a positive pressure at the filter outlet side, the present inventors have conducted further studies on the relationship between a head drop and a flow rate by variously changing the upstream head drop, the downstream head drop, and the total of the upstream head drop and the downstream head drop. As a result, the inventors have found a seemingly mysterious phenomenon that when the head drop is increased in order to increase the flow rate, the flow rate no more increases and remains constant in a certain range of conditions and, if the head drop continues to be further increased, the flow rate again starts to increase.

The present inventors have undertaken continued extensive studies giving attention to this phenomenon. As a result, the inventors have found that the pressure at the outlet side can be maintained positive, if the combination of hydrodynamic characteristics in the flow channel such as the upstream head drop of the filter, the downstream head drop, the total head drop of the upstream head drop, the downstream head drop, and the head drops of the liquid inlet port and outlet port of the filter, the resistance in the upstream side flow channel, the resistance in the downstream side flow channel, and the resistance of the filter are appropriately selected, and that if the combination of hydrodynamic characteristics in the flow channel is selected so that the pressure at the outlet side is maintained at 0 mmHg or higher above atmospheric pressure, not only a favorable flow rate can be obtained, but also removability of undesired components can be increased as compared with the case where a combination making the pressure negative is selected. These findings have led to the completion of the present invention.

Specifically, the present invention provides a filtering method and a filtering system for a liquid characterized by maintaining the pressure at the outlet side of a filter at 0 mmHg or more above atmospheric pressure, when filtering the liquid such as blood by gravity or by using a feed pump through a filter comprising a flexible housing having an inlet port and outlet port for the liquid and a sheet-like filter element for removing undesired components from the liquid, the inlet port being separated from the outlet port by the filter element.

The present invention further provides a method and system for filtering a liquid comprising appropriately selecting the combination of hydrodynamic characteristics of the filter and the flow channel on the upstream and downstream sides of the filter so that the pressure at the outlet side of the filter may be 0 mmHg or more above atmospheric pressure.

In the present invention, if the pressure at the outlet side of the filter is maintained 0 mmHg or more above atmospheric pressure, the outlet side flexible housing does not receive a force to cause it to adhere to the filter element, whereby a space for a liquid to flow between the outlet side flexible housing and the filter element can be ensured without providing a spacer between them, and a desired flow rate can be acquired. In addition, the situation in which a part of filter element cannot substantially allow a liquid to flow therethrough due to adhesion of the outlet side housing can be avoided. Specifically, generating the un-uniform flow due to utilizing only a part of filter element can be avoided. Increasing a flow rate is commonly known to decrease removing performance. However, the results obtained by the present invention go seemingly against this common sense. Specifically, supposing a system having a certain total head drop of the upstream side head drop and the downstream side head drop, an operation in which the outlet side pressure is positive not only exhibits a desired flow rate but also can achieve better removal performance as compared with an operation in which the outlet side pressure is negative. Preventing un-uniform flow ensures the maximum utilization of the filter element and results in an increased flow rate and improved removal performance at the same time.

BEST MODE FOR CARRYING OUT THE INVENTION

Figure 1:
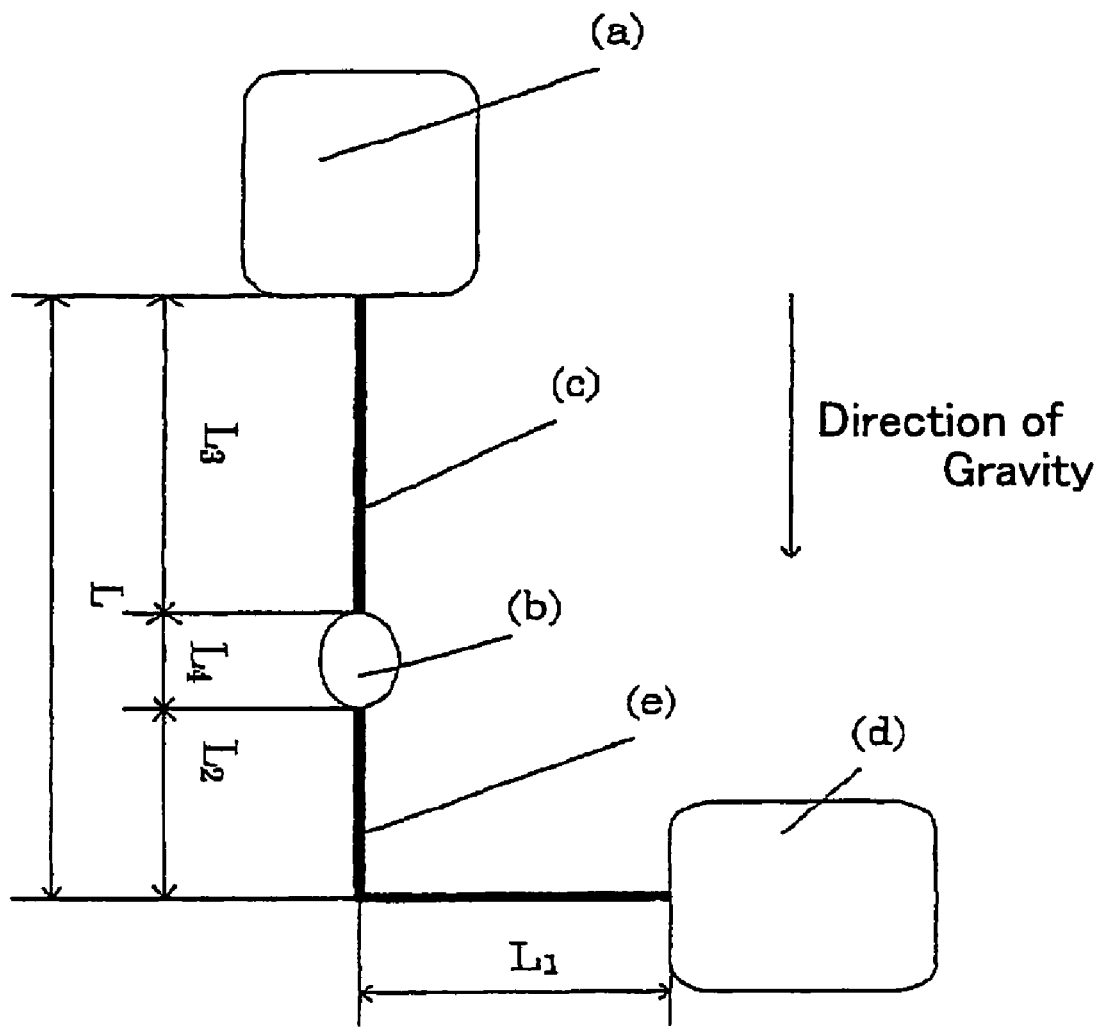
FIG. 1 is a view illustrating an apparatus used for the liquid filtering method of the present invention.

The present invention will be explained in more detail in the following description, which is not intended to be limiting of the present invention.

Specifically, the present invention relates to a filtering method and a filtering system of a liquid characterized by maintaining the pressure at the outlet side of a filter at 0 mmHg or more above atmospheric pressure, when filtering the liquid by gravity or by using a feed pump through a filter comprising a flexible housing having an inlet port and outlet port for the liquid and a sheet-like filter element, the inlet port being separated from the outlet port by the filter element.

A reservoir to store a liquid to be filtered is connected on the upstream side of the filter and a recovery vessel to collect the filtered liquid is connected on the downstream side.

The flexible housing used in the present invention includes, but is not limited to conventionally known filter housings described in the above Japanese Patent Application Laid-open No. 07-267871 and WO 95/17236, for example.

Although any commonly known sheet-like filter element can be used in the present invention, as sheet-like filter elements, fibrous aggregates such as non-woven fabric and porous materials such as sponge can be given. When blood is filtered using the filtering method of the present invention, the filter material may be coated with a hydrophilic polymer to improve wettability of the filter with blood. When the filtering method of the present invention is used for selectively removing leukocytes from blood, a filter material may be coated with a polymer promoting attachment of leukocytes to the filter.

From the viewpoint of avoiding imperfect welding of the filter and a complicated manufacturing process, it is preferable that the filter outlet side not be provided with a spacer for securing a flow channel. Specifically, it is not desirable to use either one or both of the filter of which the internal surface of the outlet side flexible housing has been processed to provide irregularity as a spacer for securing a flow channel at the filter outlet side and the filter in which a tube is inserted between the outlet side flexible housing and the sheet-like filter as a spacer for securing a flow channel at the filter outlet side.

The pressure at the outlet side in the present invention refers to a pressure above atmospheric pressure at the point close to the liquid outlet port of the filter. This pressure can be measured using a manometer connected at the point close to the liquid outlet port via a T-letter tube or the like when at least the upstream side flow channel, filter, and the downstream side flow channel are filled with a liquid.

To maintain the pressure at the outlet side 0 mmHg or more above atmospheric pressure, the hydrodynamic characteristics in the filter and the flow channel on the upstream side or the downstream side of the filter are appropriately selected and combined. The hydrodynamic characteristics include the upstream head drop, the downstream head drop, the total head drop of the upstream head drop, the downstream head drop, and the head drops of the liquid inlet port and outlet port of the filter, the resistance in the upstream side flow channel, the resistance in the downstream side flow channel, and the resistance of the filter.

In the present invention, the upstream side flow channel of the filter refers to a flow channel between the reservoir to store the liquid to be filtered and the inlet port of the filter, and the downstream side flow channel refers to a flow channel between the outlet port of the filter and the recovery vessel to collect the filtered liquid.

The head drop in the present invention refers to the vertical direction component of a distance between two points. For example, when the upstream side flow channel is vertically (in the lower direction) suspended from the reservoir bag for storing a liquid to be filtered and the tip of the flow channel is connected with the filter inlet port, the lengths of the upstream side flow channel and the upstream side head drop are substantially the same. When the filter position is raised, however, the length of the upstream side flow channel does not change, but the upstream side head drop decreases.

The flow channel resistance, filter resistance, and the like vary according to the viscosity of the liquid to be filtered, the coefficient of friction inside the flow channel, the inside diameter and cross section area of the flow channel, and the resistance coefficient and effective cross section area of the filter.

Although the combination of these characteristics to maintain the pressure at the outlet side of the filter 0 mmHg or more depends on operational conditions such as the viscosity of the liquid to be filtered, the desired flow rate and removal rate, the pressure resistant characteristics of the filter, and the maximum allowable head drop, the following methods can be applied, for example. One method is to maintain the resistance of the downstream side flow channel larger than the resistance of the upstream side flow channel by having the upstream side head drop larger than the downstream side head drop, the downstream side flow channel longer than the length of the upstream side flow channel, the internal diameter of the downstream side flow channel smaller than the internal diameter of the upstream side flow channel, and the like.

Another method is to increase the resistance of the downstream side flow channel against the force of the liquid to flow down due to the head drop on the downstream side by loosening the downstream side flow channel by bundling or coiling the downstream side flow channel using a solvent or high frequency, by binding the downstream side flow channel using a string or an other things, or by simply decreasing the head drop to a length shorter than the total flow channel length during filtration, by shortening internal diameter of a part of the downstream side flow channel by squeezing a part of the flow channel using a clamp, or by using a pipe with a small diameter as a part of the flow channel. In addition, the same effect as that obtained by increasing the resistance of the downstream side flow channel can be obtained by increasing the resistance of the outlet side by decreasing the nozzle diameter at the outlet port of the filter, for example. In this instance, the pressure at the outlet side can be measured by providing a flow channel connecting with the inside of the housing in part of the flexible housing on the outlet side of the filter and connecting a pressure gauge to this flow channel. The degree of the head drop increase or resistance increase to maintain the pressure of the outlet side of the filter 0 mmHg or higher can be appropriately determined by experiments. Furthermore, the liquid filtering system of the present invention may be provided with a bypass flow channel to connect the intermediate of the downstream side flow channel of the filter or the filtered liquid recovery bag with the intermediate of the upstream side flow channel of the filter or the reservoir bag for the liquid to be filtered. The bypass flow channel can exhaust air from the filter. Specifically, the air pushed forward to the recovery bag from the filter can be exhausted through the bypass flow channel. In addition, the head drop between the reservoir bag and the recovery bag can be controlled by adjusting the length of the bypass flow channel. The bypass flow channel should be provided with a flow channel controlling member to prevent the liquid to be processed from directly flowing into the recovery bag without passing through the filter. As the flow channel controlling member, a check valve, breakable connector, plastic clamp, forceps, or the like can be used. The length of the bypass flow channel must be shorter than the total of the length of the upstream side flow channel located between the upper and lower joints of the bypass flow channel and the length of the filter and the downstream side flow channel.

It is also possible to keep the pressure at the outlet side 0 mmHg or more above atmospheric pressure using the action of a feed pump. Substantially the same effect as that obtained by increasing the resistance of the downstream side flow channel can be obtained by installing a feed pump in the downstream side flow channel of the filter and controlling the feed rate of the liquid by the pump. The same effect as that obtained by increasing the resistance of the downstream side flow channel can also be obtained by increasing the feed rate of the liquid using a feed pump installed in the upstream side flow channel.

In addition, it is possible to install a feed pump in both the upstream side and downstream side of the flow channel of filter to freely control the pressure inside the filter by controlling the feed rate of the respective pumps.

Alternatively, a pressure gauge may be installed in the flow channel branching from the outlet side of the filter to control the feed pump while detecting the pressure at the outlet side, whereby it is possible to constantly maintain the pressure at the outlet side at 0 mmHg or more above atmospheric pressure.

In the present invention, the pressure at the outlet side can also be maintained at 0 mmHg with respect to atmospheric pressure not only by controlling the feed rate of the pump, but also by controlling the head drop and/or the length of the flow channel at the same time.

In filtering a liquid by gravity, the combination of characteristics can be selected so as to satisfy the following formula (2) as a more detailed example for controlling the pressure at the outlet side by means of the head drop and the flow channel length.

The pressure at the outlet side Px (unit: Pa) can be determined by the following energy conservation equation:

$$Px/\gamma = P\infty/\gamma + (\lambda_{low}(L_1+L_2)Q^2)/(d_{low} \cdot 2g \cdot A_{low}^2) - L_2 \quad (1)$$

wherein $P\infty$ is atmospheric pressure and $\gamma$ is the specific gravity of the liquid.

The following formula (2) was derived by modifying the above formula (1) and based on experimental data, $$X \text{ value} = (\lambda_{low}(L_1+L_2)Q^2)/(d_{low} \cdot 2g \cdot A_{low}^2)/L_2 > 1.5 \quad (2)$$

wherein, $$Q = (-C_3 + (C_3^2 + 4(L_2+L_3+L_4)(C_1+C_2+1/(2g \cdot A_{low}^2)))^{1/2})/2(C_1+C_2+1/(2g \cdot A_{low}^2))$$

$$C_1 = \lambda_{low}(L_1+L_2)/(d_{low} \cdot 2g \cdot A_{low}^2)$$

$$C_2 = (\lambda_{up} \cdot L_3)/(d_{up} \cdot 2g \cdot A_{up}^2)$$

$$C_3 = \mu K/A_f$$

and, $\lambda_{low}$ and $\lambda_{up}$ are respectively coefficients of friction (dimensionless) for the downstream side flow channel and the upstream side flow channel, $L_1+L_2$ are the length of the downstream side flow channel (unit: m), $L_1$ is a length of the flow channel (unit: m) that does not contribute to the downstream side head drop in the downstream side flow channel due to the horizontal arrangement or the like, $L_2$ is the head drop of the downstream side (unit: m), $L_3$ is the length of the upstream side flow channel (same as the head drop of the upstream side, unit: m), $L_4$ is the head drop due to the distance between the filter inlet port and outlet port (unit: m), $d_{low}$ and $d_{up}$ are respectively the internal diameters of the downstream side flow channel and the upstream side flow channel (unit: m), g is the gravitational acceleration (9.8 m/sec²), $A_{low}$ and $A_{up}$ are respectively the cross-section areas of the downstream side flow channel and the upstream side flow channel (unit: m²), $\mu$ is the viscosity of the liquid flowing through the filter (unit: Pa·s), K is the resistance coefficient of the filter (unit: 1/Pa), and $A_f$ is the effective filtration area of the filter (unit: m²).

The coefficient of friction $\lambda$ of the flow channel in the present invention can be measured as follows. A flow channel with a length of 2 m and an internal diameter of d m is horizontally placed and T-tubes are installed at 0.5 m and 1.5 m from the inlet port to connect pressure gauges 1 and 2. An aqueous solution of PVP (pH 3.6) with a viscosity of 21.4 mPa·s and a density of 1028.8 kg/m³ was prepared and caused to flow through the flow channel at a flow rate of 15 ml/min using a pump or the like that does not substantially cause pulsation. After the pressures indicated by the pressure gauges 1 and 2 were stabilized, the respective values (unit: Pa) were recorded and the difference of the recorded pressure values was multiplied by $(1.92 \times 10^{10}) \times d^5$ (unit: 1/Pa) to obtain the value for $\lambda$.

To determine the resistance coefficient K of the filter, the air permeability test was carried out for each sheet forming the sheet-like filter according to the JIS L-1096, 6.27.1A. The reciprocal number of the determined result (unit: cc/cm²/sec) was multiplied by a coefficient of $6.638 \times 10^4$ (unit: sec/cm/Pa) to calculate the value K (unit: 1/Pa) for each sheet. The total of the K values for all sheets was taken as the resistance coefficient K of the filter.

The effective filtration area $A_f$ of the filter in the present invention indicates the filtration area when the entire filter element is effectively utilized. This is the area inside the sealed region formed near the circumference of the filter element.

One embodiment of the apparatus for carrying out the liquid filtering method of the present invention is schematically shown in the Figure. A reservoir bag (a) for storing a liquid to be filtered and the inlet port of a filter (b) using a flexible housing are connected by an upstream side flow channel (c) with an internal diameter of $d_{up}$ to provide an upstream side head drop equivalent to the length $L_3$ of the upstream side flow channel. A part (length: $L_1$) of the downstream side flow channel is placed horizontally with respect to the floor, providing a downstream side head drop equivalent to the remainder of the downstream side flow channel of length $L_2$. The liquid inlet port and outlet port of the filter (b) are provided with an interval in the vertical direction, wherein the distance between the inlet port and the outlet port corresponds to the head drop $L_4$ in this section. In this instance, the hydrodynamic characteristics of the filter such as the resistance coefficient K and effective filtration area of the filter, the viscosity of the liquid to be filtered, the values $L_1$, $L_2$, $L_3$, $L_4$, $d_{low}$, $d_{up}$, and the like are appropriately selected and combined so that the pressure at the outlet side of the filter is 0 mmHg or more above atmospheric pressure. In practice, however, these characteristics of the filter and the liquid to be filtered may be subject to various restrictions and unchangeable in many cases. In such a case, a practical method is to appropriately select and combine the hydrodynamic characteristics of the filter such as $L_1$, $L_2$, $L_3$, $L_4$, $d_{low}$, and $d_{up}$ taking due consideration to the other characteristics of the filter and the liquid to be filtered.

In addition, in many cases there is an operationally allowable ceiling value for the total head drop (L) of the upstream side head drop, the head drop between the inlet port and outlet port of the filter, and the downstream side head drop at the site where the filtration is practically conducted. Moreover, the case in which the liquid to be filtered has a wide temperature range and, accordingly, the viscosity of the liquid is largely different, is not rare. Therefore, taking this situation into consideration, it is preferable that the system is designed so that the user can appropriately select suitable values for $L_1$, $L_2$, and $L_3$ according to the viscosity of the liquid.

The term "liquid filtering system" in the present invention includes an apparatus for filtering a liquid. The filtering system of the present invention comprises a flexible housing having an inlet port and outlet port for a liquid, a sheet-like filter element for removing undesired components from the liquid, a filter having a liquid inlet port and an outlet port separated from each other by the filter element, a reservoir bag for storing the liquid to be filtered, an upstream side flow channel connecting the filter inlet port with the reservoir bag, a filtered liquid recovery bag, a downstream side flow channel connecting the filter outlet port with the recovery bag, and other components. These parts are connected so that the pressure at the outlet side may be 0 mmHg or more above atmospheric pressure when filtering the liquid in the reservoir bag by gravity and collecting the filtered liquid in the recovery bag.

Alternatively, the filtering system comprises at least a flexible housing having an inlet port and outlet port for a liquid, a sheet-like filter element for removing undesired components from the liquid, a filter having a liquid inlet port and an outlet port separated from each other by the filter element, an upstream side flow channel connected to the filter inlet port, a filtered liquid recovery bag, a downstream side flow channel connecting the filter outlet port with the recovery bag, and a feed pump installed in the upstream side flow channel and/or the downstream side flow channel. The system is designed so that the feed rate of the feed pump installed in the upstream side flow channel and/or the downstream side flow channel can be controlled to ensure that the pressure at the filter outlet side is 0 mmHg or more above atmospheric pressure when a liquid is filtered.

EXAMPLES

The leukocyte-removing filter of the present invention will now be described in detail by way of examples, which should not be construed as limiting the present invention.

Examples 1-3 and Comparative Examples 1-9

A filter (K=4445.5 Pa$^{-1}$, Af=43.5×10$^{-4}$ m$^2$) comprising a flexible housing having a liquid inlet port and outlet port and a sheet-like filter element, but not substantially comprising a spacer to prevent the outlet side housing from adhering to the filter element was used. The liquid inlet port was connected to a reservoir bag for storing a liquid to be filtered via an upstream side flow channel with a length of 1.0 m. The liquid outlet port of the filter was connected to a filtered liquid recovery bag via a downstream side flow channel with a length of 1.0 m. A tube for pressure measurement and a pressure gauge (manufactured by Copal Electronics Corp.) were connected close to the liquid outlet port of the filter via T-tube. A sheet with a thickness of 0.37 mm made of soft polyvinyl chloride was used as the flexible housing and a tube with an internal diameter of 2.9 mm and external diameter of 4.2 mm made of soft polyvinyl chloride was used as the upstream side flow channel, the downstream side flow channel, and the tube for pressure measurement. In preparing the filter, the liquid inlet port and outlet port were arranged to have a head drop of 0.1 m, and an effective filtration area of 43.5×10$^{-4}$ (m$^2$) was provided. As the filter element, six sheets of polyester nonwoven fabric with an air permeability of 237.3 (cc/cm$^2$/sec) and a thickness of 0.2 mm, two sheets of polyester nonwoven fabric with an air permeability of 8.4 (cc/cm$^2$/sec) and a thickness of 0.4 mm, 25 sheets of polyester nonwoven fabric with an air permeability of 8.8 (cc/cm$^2$/sec) and a thickness of 0.23 mm, and one sheet of polyester nonwoven fabric with an air permeability of 237.3 (cc/cm$^2$/sec) and a thickness of 0.2 mm, were stacked in that order from the liquid inlet port to the outlet port, and used.

The total of the upstream side head drop, the head drop between the filter inlet port and outlet port, and the downstream side head drop was set at 1.0 m. As a liquid to be filtered, an aqueous solution of polyvinyl pyrrolidone (molecular weight: 390,000) adjusted to a viscosity of 21.4 mPa·s (24.7° C.) and pH 3.6 was filled into the reservoir bag for storing the liquid to be filtered and caused to flow by gravity at room temperature. The upstream side head drop was adjusted in units of 5 cm by moving the filter up and down so that the pressure of the filter outlet side became positive in Examples 1-3 and negative in Comparative Examples 1-9. The period of time required for 150 ml of the liquid to be filtered was measured. The filtration rate (ml/min) was calculated based on the measured period of time. In Examples 1-3 in which the pressure of the filter outlet side was kept positive, the filtering section of the filter element was for all practical purposes completely effectively used, constantly showing the maximum flow rate irrespective of the pressure at the outlet side. In Comparative Examples 1-9 in which the pressure of the filter outlet side was negative, a part of the filter element was not effectively used, with the flow rate decreasing according to the decrease of the pressure at the outlet side. However, no further decrease in the flow rate was seen when the pressure of the filter outlet side decreased to −27 mmHg or less. The reason why the flow rate ceased decreasing was believed to be because if the negative pressure at the outlet side continues to decrease until the degree of un-uniform flow reaches worst, no more un-uniform flow occurs and the flow rate does not decrease any more. The results are shown in Table 1.

Reference Examples 1-2

The same filtration experiments as in Example 1 and Comparative Example 9 were carried out, except that a filter using a hard housing made of polycarbonate was used instead of the flexible housing. The head drop between the liquid inlet port and outlet port of the hard housing was 0.15 m. When the filter fabricated from a hard housing was used, no substantial change in the flow rate was seen, regardless whether the pressure at the outlet side was negative or positive. The results obtained in Examples 1-3, Comparative Examples 1-9, and Reference Example are collectively shown in Table 1.

TABLE 1

|  | Example | | | Comparative Example | | | |
| --- | --- | --- | --- | --- | --- | --- | --- |
|  | 1 | 2 | 3 | 1 | 2 | 3 | 4 |
| Total head drop (cm) | 100 | 100 | 100 | 100 | 100 | 100 | 100 |
| Length of upstream side flow channel (cm) | 100 | 100 | 100 | 100 | 100 | 100 | 100 |
| Upstream side head drop (cm) | 75 | 70 | 65 | 60 | 55 | 50 | 45 |
| Length of downstream side flow channel (cm) | 100 | 100 | 100 | 100 | 100 | 100 | 100 |
| Downstream side head drop (cm) | 15 | 20 | 25 | 30 | 35 | 40 | 45 |
| X value | 2.56 | 1.92 | 1.54 | 1.28 | 1.10 | 0.96 | 0.85 |
| Outlet side pressure (mmHg) | 6 | 3 | 0 | −5 | −8 | −15 | −18 |
| Flowrate (ml/min) | 20 | 19 | 19 | 17 | 15 | 14 | 14 |

|  | Comparative Example | | | | | Reference Example | |
| --- | --- | --- | --- | --- | --- | --- | --- |
|  | 5 | 6 | 7 | 8 | 9 | 1 | 2 |
| Total head drop (cm) | 100 | 100 | 100 | 100 | 100 | 100 | 100 |
| Length of upstream side flow channel (cm) | 100 | 100 | 100 | 100 | 100 | 100 | 100 |
| Upstream side head drop (cm) | 40 | 35 | 30 | 25 | 20 | 75 | 20 |
| Length of downstream side flow channel (cm) | 100 | 100 | 100 | 100 | 100 | 100 | 100 |
| Downstream side head drop (cm) | 50 | 55 | 60 | 65 | 70 | 15 | 70 |
| X value | 0.77 | 0.70 | 0.64 | 0.59 | 0.55 | 2.56 | 0.55 |
| Outlet side pressure (mmHg) | −23 | −27 | −31 | −35 | −40 | 6 | −40 |
| Flow rate (ml/min) | 13 | 12 | 13 | 13 | 13 | 19 | 20 |

Example 4 and Comparative Examples 10-11

The filtration experiments were carried out in the same manner as in Example 1, except that the length of the upstream side flow channel (same as the upstream side head drop) was fixed at 75 cm (Example 4), 55 cm (Comparative Example 10), or 45 cm (Comparative Example 11) and an aqueous solution of polyvinyl pyrrolidone (viscosity: 28.3 mPa·s) in which fluorescent particles (average diameter 2.5 μm) were suspended at a concentration of 6.0×10⁶ (particles/ml) was used, and the pressure at the outlet side of each filter, flow rate and removal rate of particles were determined.

The removal rate of particles was determined as logarithmic removal rate that was obtained by dividing the fluorescence intensity of the first 150 ml filtrate by the fluorescence intensity of the liquid before filtration and multiplying the logarithmic value of the quotient by −1. In actual measuring the fluorescence intensity, the liquid before filtration and the filtrate were diluted or condensed as required. The fluorescence intensity was determined by adjusting the measured value using a dilution rate or concentration rate. The logarithmic removal rate was calculated using the resulting fluorescence intensity. Example 4 using a positive pressure for the outlet side exhibited a higher flow rate and higher removal rate as compared with Comparative Examples 10 and 11 using a same negative pressure for the outlet side. The results are shown in Table 2.

TABLE 2

|  | Example | Example Comparative | |
| --- | --- | --- | --- |
|  | 4 | 10 | 11 |
| Total head drop (cm) | 100 | 100 | 100 |
| Length of upstream side flow channel (cm) | 75 | 55 | 45 |
| Upstream side head drop (cm) | 75 | 55 | 45 |
| Length of downstream side flow channel (cm) | 100 | 100 | 100 |
| Downstream side head drop (cm) | 15 | 35 | 45 |
| X value | 2.63 | 1.24 | 1.02 |
| Outlet side pressure (mmHg) | 9 | −4 | −14 |
| Flow rate (ml/min) | 14.2 | 13.1 | 12.0 |
| Logarithmic removal rate of particles (Log) | 3.30 | 2.52 | 2.41 |

Examples 5-6 and Comparative Examples 12-15

A filter (K=6788.3 Pa⁻¹, $A_f$=43.5×10⁻⁴ m²) comprising a flexible housing was used. The liquid inlet port was connected with a reservoir bag for a liquid to be filtered via an upstream side flow channel with a length of 0.5 m. The liquid outlet port of the filter was connected to a filtered liquid recovery bag via a downstream side flow channel with a length of 1.0 m. In addition, a pipe for pressure measurement and a pressure gauge (manufactured by Copal Electronics Corp.) were connected close to the liquid outlet port of the filter via a T-tube. A sheet with a thickness of 0.37 mm made of soft polyvinyl chloride was used as the flexible housing and a tube with an internal diameter of 2.9 mm and external diameter of 4.2 mm made of soft polyvinyl chloride was used as the upstream side flow channel, the downstream side flow channel, and the tube for pressure measurement. In preparing the filter, the liquid inlet port and outlet port were arranged to have a head drop of 0.1 m and an effective filtration area was adjusted 43.5×10⁻⁴ (m²). As the filter element, four sheets of polyester nonwoven fabric with an air permeability of 237.3 (cc/cm²/sec) and a thickness of 0.2 mm, one sheet of polyester nonwoven fabric with an air permeability of 8.4 (cc/cm²/sec) and a thickness of 0.4 mm, 32 sheets of polyester nonwoven fabric with an air permeability of 7.1 (cc/cm²/sec) and a thickness of 0.20 mm, one sheet of polyester nonwoven fabric with an air permeability of 8.4 (cc/cm²/sec) and a thickness of 0.4 mm, and four sheets of polyester nonwoven fabric with an air permeability of 237.3 (cc/cm²/sec) and a thickness of 0.2 mm, were stacked in that order from the liquid inlet port to the outlet port, and used.

The reservoir bag for a liquid to be filtered was suspended from a hook. As a liquid to be filtered, an aqueous solution of polyvinyl pyrrolidone (molecular weight: 390,000) adjusted to a viscosity of 21.4 mPa·s (24.7° C.) and pH 3.6 was filled into the reservoir bag and caused to flow by gravity at room temperature. The total head drop was adjusted in the range from 70-120 cm in units of 10 cm by adjusting the height of the hook. The period of time required for 150 ml of the liquid to be filtered was measured. The filtration rate (ml/min) was calculated based on the measured period of time. As a result, the pressure at the outlet side was positive in Examples 5-6 and negative in Comparative Examples 12-15. The pressure value at the outlet side was confirmed that the effective utilization rate of the filtering section even in systems with the same flow channel specification varies by changing only the total head drop. The results are shown in Table 3.

Example 10

The filtration experiment was carried out in the same manner as in Comparative Example 8, except that the distance between the reservoir bag for a liquid to be filtered and the filtered liquid recovery bag was adjusted to 100 cm by bundling a part of the downstream side flow channel with a length of 1.0 m using strings in the form of a coil with a diameter of 10 cm. The pressure at the outlet side and the filtration rate were measured. The results are shown in Table 5.

Example 11

The filtration experiment was carried out in the same manner as in Comparative Example 8, except that the distance between the reservoir bag for a liquid to be filtered and the recovery bag for the filtrate was adjusted to 100 cm by connecting the reservoir bag and the recovery bag using a string.

The pressure at the outlet side and the filtration rate were measured. The results are shown in Table 5.

TABLE 3

|  | Example | | Comparative Example | | | |
| --- | --- | --- | --- | --- | --- | --- |
|  | 5 | 6 | 12 | 13 | 14 | 15 |
| Total head drop (cm) | 70 | 80 | 90 | 100 | 110 | 120 |
| Length of upstream side flow channel (cm) | 50 | 50 | 50 | 50 | 50 | 50 |
| Upstream side head drop (cm) | 50 | 50 | 50 | 50 | 50 | 50 |
| Length of downstream side flow channel (cm) | 100 | 100 | 100 | 100 | 100 | 100 |
| Downstream side head drop (cm) | 10 | 20 | 30 | 40 | 50 | 60 |
| X value | 2.69 | 1.60 | 1.23 | 1.05 | 094 | 0.87 |
| Outlet side pressure (mmHg) | 7 | 1 | −6 | −11 | −16 | −21 |
| Flow rate (ml/min) | 7.8 | 8.4 | 8.9 | 9.1 | 9.0 | 9.1 |

Examples 7-9 and Comparative Examples 16-18

The filtration experiments were carried out in the same manner as in Examples 5-6 and Comparative Examples 12-15, except that the liquid inlet port of the filter comprising a flexible housing was connected with a reservoir bag for a liquid to be filtered via an upstream side flow channel with a length of 0.75 m and the total head drop was adjusted in the range from 90-140 cm in units of 10 cm, and the pressure at the outlet side and the filtration rate were measured. The results are shown in Table 4.

Examples 12-14

The filtration experiment was carried out in the same manner as in Comparative Example 8, except that the flow channel was narrowed in the order of Examples 12, 13, and 14 using a roller clamp provided on the downstream side flow channel at about 15 cm below the filter. The pressure at the outlet side and the filtration rate were measured. The results are shown in Table 5.

TABLE 4

|  | Example | | | Comparative Example | | |
| --- | --- | --- | --- | --- | --- | --- |
|  | 7 | 8 | 9 | 16 | 17 | 18 |
| Total head drop (cm) | 90 | 100 | 110 | 120 | 130 | 140 |
| Length of upstream side flow channel (cm) | 75 | 75 | 75 | 75 | 75 | 75 |
| Upstream side head drop (cm) | 75 | 75 | 75 | 75 | 75 | 75 |
| Length of downstream side flow channel (cm) | 100 | 100 | 100 | 100 | 100 | 100 |
| Downstream side head drop (cm) | 5 | 15 | 25 | 35 | 45 | 55 |
| X value | 6.55 | 2.48 | 1.67 | 1.32 | 1.13 | 1.01 |
| Outlet side pressure (mmHg) | 11 | 9 | 2 | −7 | −13 | −18 |
| Flow rate (ml/min) | 9.2 | 9.4 | 9.8 | 10.1 | 10.0 | 9.8 |

TABLE 5

|  | Example | | | | |
| --- | --- | --- | --- | --- | --- |
|  | 10 | 11 | 12 | 13 | 14 |
| Total head drop (cm) | 100 | 100 | 140 | 140 | 140 |
| Length of upstream side flow channel (cm) | 75 | 75 | 75 | 75 | 75 |
| Upstream side head drop (cm) | 75 | 75 | 75 | 75 | 75 |
| Length of downstream side flow channel (cm) | 100 | 100 | 100 | 100 | 100 |
| Downstream side head drop (cm) | 15 | 15 | 55 | 55 | 55 |
| Outlet side pressure (mmHg) | 12 | 11 | 25 | 36 | 48 |
| Flow rate (ml/min) | 9.0 | 9.2 | 7.9 | 5.7 | 3.5 |

INDUSTRIAL APPLICABILITY

As described above, in a filter using a flexible housing, if the combination of hydrodynamic characteristics in the flow channel is appropriately selected to maintain the pressure at the filter outlet side at 0 mmHg or more, the entire filter element can be effectively utilized, resulting in a high flow rate and high removal rate at the same time, without installing a spacer to prevent adhesion of the outlet side housing to the filter element.

The invention claimed is:

1. In a method of filtering blood using a filter comprising a flexible housing having an inlet port and outlet port, said inlet port being separated from the outlet port by a sheet-like filter element, said sheet-like filter element removing undesired components from the blood while feeding the blood by gravity, the method including:
    connecting the inlet port to a reservoir containing blood;
    connecting the outlet port to a recovery vessel;
    feeding the blood from the reservoir to the filter by gravity;
    adjusting at least one filtration parameter so that a pressure at an outlet side of the filter becomes 0 mmHg or more above atmospheric pressure;
    maintaining a pressure at the outlet side of the filter at 0 mmHg or more above atmospheric pressure throughout filtration by adjusting said at least one filtration parameter; and
    collecting filtered blood in the recovery vessel.

2. The method according to claim 1, wherein the pressure at the outlet side of the filter is maintained at 0 mmHg or more above atmospheric pressure by a combination of altering hydrodynamic characteristics of the filter and adjusting a length of a flow channel on an upstream side or a downstream side of the filter.

3. The method according to claim 2, wherein the pressure at the outlet side of the filter is maintained at 0 mmHg or more above atmospheric pressure by adjusting a combination of the upstream head drop of the filter, the downstream head drop of the filter, the total head drop of the upstream head drop, the downstream head drop and the head drop between the liquid inlet port and outlet port of the filter, the resistance of the upstream side flow channel, the resistance of the downstream side flow channel, and the resistance of the filter.

4. The method according to claim 3, wherein the pressure at the outlet side of the filter is maintained at 0 mmHg or more above atmospheric pressure by maintaining the head drop on the upstream side of the filter larger than the head drop on the downstream side.

5. The method according to claim 1, wherein the filter does not comprise a spacer for securing a flow channel at the outlet side of the filter.

6. The method according to claim 1, wherein a filter of which the outlet side flexible housing has not been processed to provide irregularity as a spacer for securing a flow channel at the filter outlet side and/or a filter in which a tube is not inserted between the outlet side flexible housing and the sheet-like filter as a spacer for securing a flow channel at the filter outlet side are/is used.

7. The method according to claim 1, wherein the filter removes leukocytes and/or aggregates.

* * * * *